US006464663B1

(12) United States Patent
Zinger

(10) Patent No.: US 6,464,663 B1
(45) Date of Patent: Oct. 15, 2002

(54) APPLICATOR FOR APPLYING A SINGLE— OR MULTICOMPONENT FLUID AND METHOD FOR SPRAYING SUCH A FLUID

(75) Inventor: Freddy Zinger, Raanana (IL)

(73) Assignee: OMRIX Biopharmaceuticals SA, Brussels (BE)

( * ) Notice: Subject to any disclaimer, the term of this patent is extended or adjusted under 35 U.S.C. 154(b) by 0 days.

(21) Appl. No.: 09/380,844
(22) PCT Filed: Mar. 10, 1998
(86) PCT No.: PCT/EP98/01381
§ 371 (c)(1),
(2), (4) Date: Nov. 9, 1999
(87) PCT Pub. No.: WO98/40167
PCT Pub. Date: Sep. 17, 1998

(30) Foreign Application Priority Data

Mar. 11, 1997 (DE) .......................................... 197 09 896

(51) Int. Cl.[7] ............................................. A61M 37/00
(52) U.S. Cl. ........................ 604/82; 604/223; 604/207; 222/390; 239/418
(58) Field of Search ............................. 604/23, 24, 82, 604/93.01, 181, 182, 183, 186, 207, 208, 209–211, 218, 223, 224, 232, 246, 249, 257, 258–259, 518; 222/195, 326, 390, 145.5; 239/654, 143, 398, 8, 77, 417.5, 418, 548–549; 433/89–90

(56) References Cited

U.S. PATENT DOCUMENTS 3,782,380 A    1/1974   Van Der Gaast
4,264,305 A    4/1981   Rasmussen et al.
4,631,055 A  * 12/1986  Redl et al.
5,263,614 A   11/1993   Jacobsen et al.
5,612,050 A  *  3/1997  Rowe et al. ................. 424/423
5,810,885 A  *  9/1998  Zinger
6,234,994 B1 *  5/2001  Zinger

FOREIGN PATENT DOCUMENTS

EP          0548509      6/1993

* cited by examiner

Primary Examiner—Anhtuan T. Nguyen
Assistant Examiner—Catherine Serke
(74) Attorney, Agent, or Firm—Birch, Stewart, Kolasch & Birch, LLP

(57) ABSTRACT

The applicator (10) for depositing a one- or multicomponent fluid, particularly a tissue adhesive, comprises a housing (12) arranged for attachment of at least one supply container (16) for the fluid. The supply container (16) comprises a discharge opening (28) and a piston (20) for sliding displacement in the direction of said discharge opening (28). A tensioning lever (58) is pivotally supported on the housing (12), which, when manually operated, causes movement of a spring tensioning element (54) by which a spring (46) for storage of mechanical energy can be tensioned. Coupled to the spring tensioning element (54) is a drive element (66) being adapted to be driven, by the stored mechanical energy of said spring (46), in increments and which is arranged to move a press-on element (84) acting on said piston (20) for displacing it in the direction of said discharge opening (28) of said supply container (16).

18 Claims, 9 Drawing Sheets

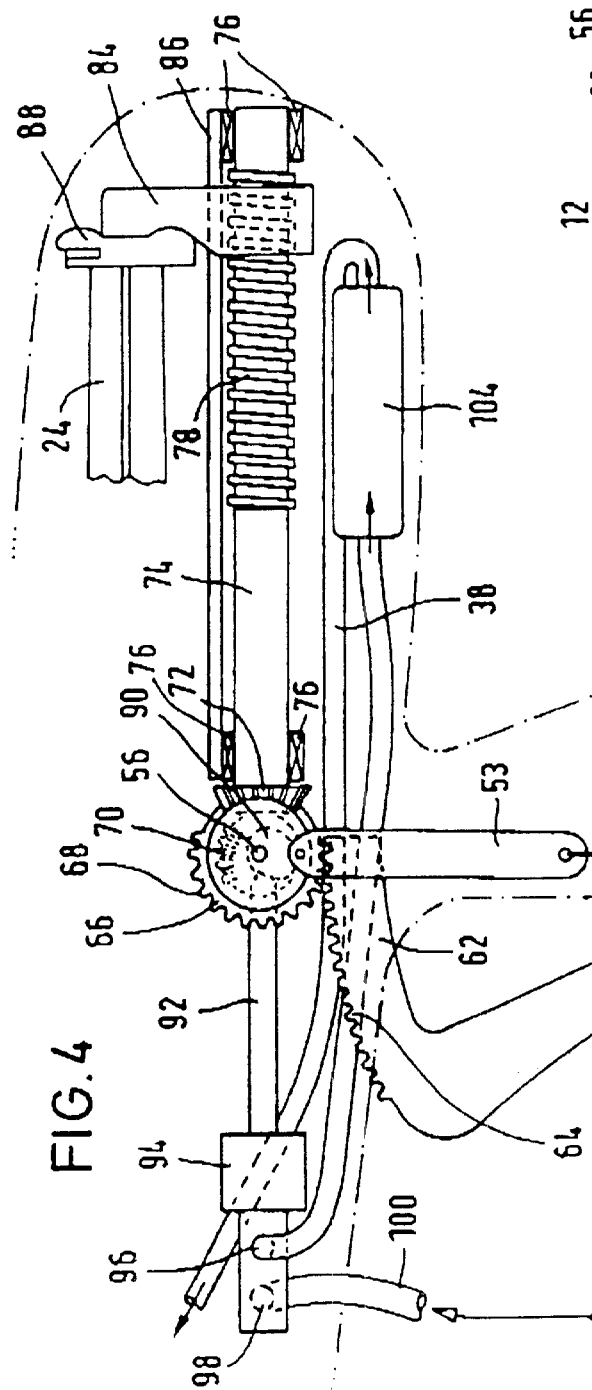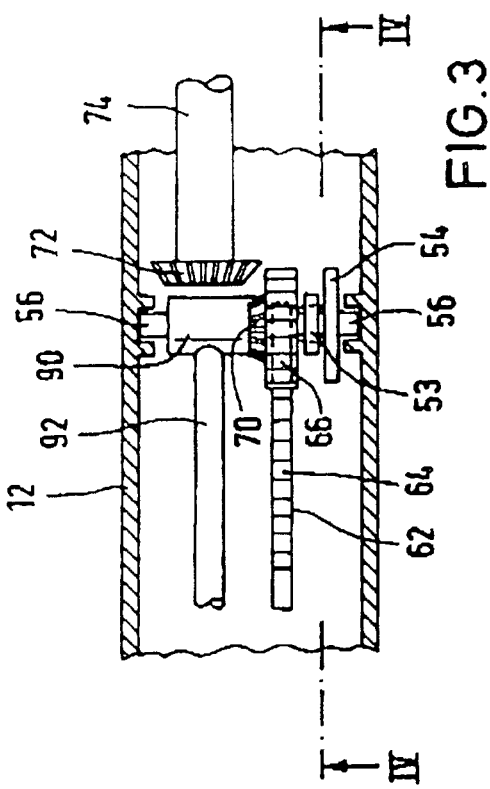

Figure 1:
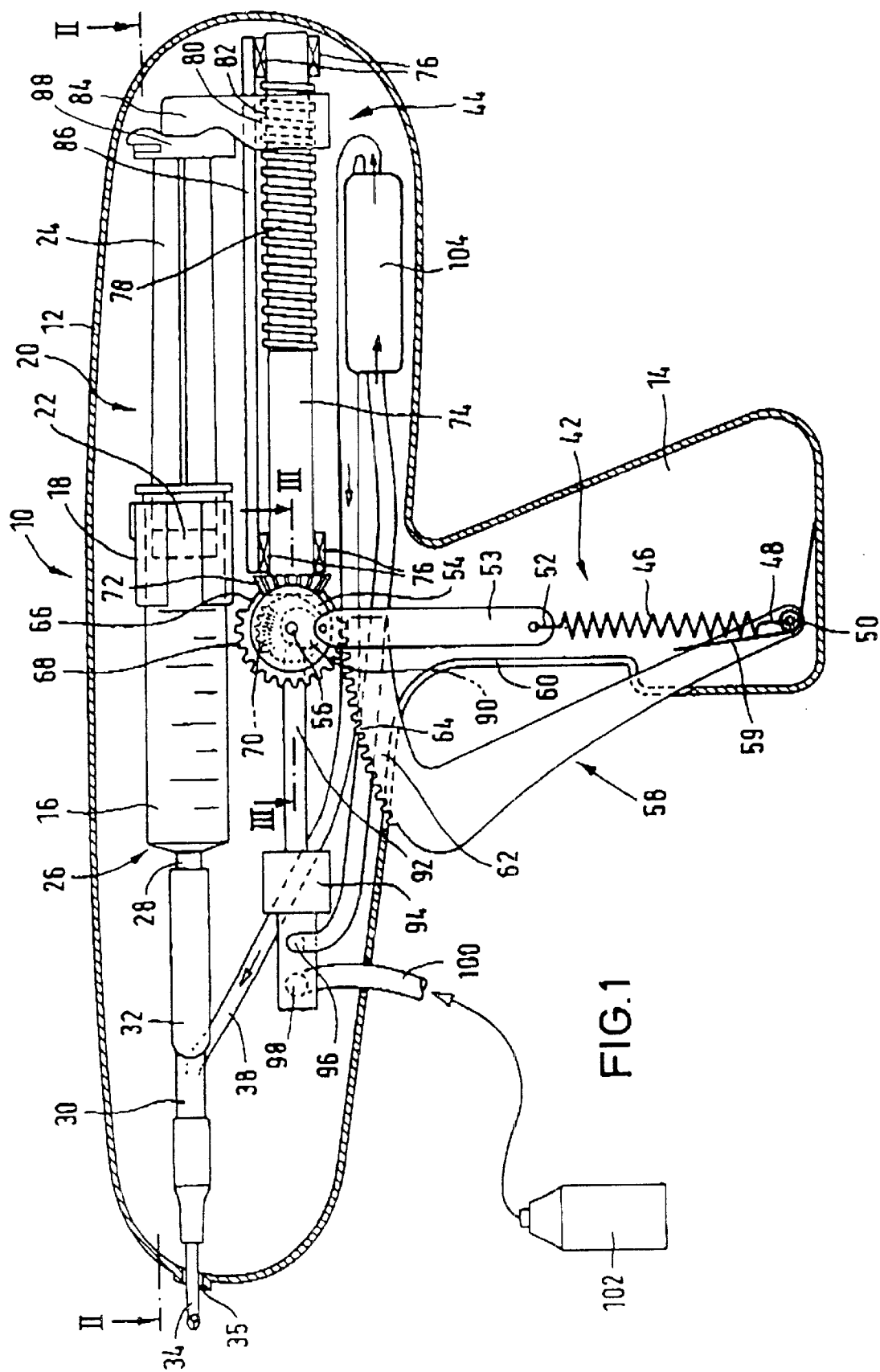

APPLICATOR FOR APPLYING A SINGLE— OR MULTICOMPONENT FLUID AND METHOD FOR SPRAYING SUCH A FLUID

This application is the national phase under 35 U.S.C. §371 of prior PCT International Application No. PCT/EP98/01381 which has an International filing date of Mar. 10, 1998 which designated the United States of America.

The invention relates to an applicator for the application of a single- or multicomponent fluid, particularly of a (single- or multicomponent) tissue glue, and a method for the application of such a fluid by spraying.

In surgery, increased use is made of tissue glues for the most various purposes. Mostly, these tissue adhesives are multicomponent tissue adhesives and normally two-component tissue adhesives which are applied by use of special applicators. Partially, in addition to the tissue glue, also a (medical) gas, e.g. $O_2$, is ejected for atomizing the discharge tissue glued so that the latter can be applied by spraying.

The production costs for tissue glue are not negligible, making it desirable to perform a dosed application of the tissue glue by use of an applicator.

In doing so, the quantity of tissue glue ejected per actuation of the applicator should be the same each time. For reasons of hygiene, it appears reasonable to design the applicator as a disposable article so that the applicator will be provided for single use only.

It is an object of the invention to provide an applicator for applying a single- or multicomponent fluid, particularly at a tissue glue, which can be manufactured at low cost and is particularly designed as a disposable article and which allows the application of an exactly dosed, always constant quantity of fluid with each use.

According to the invention, for solving the above object, there is proposed an applicator comprising a housing, at least one supply container for said fluid, adapted to be mounted to said housing, said supply container comprising a discharge opening and having arranged therein a piston for sliding displacement in the direction of said discharge opening, an energy storage means comprising a hand-operated tensioning lever, pivotally arranged on said housing, which, when moved from a rest position into a pulling position, causes movement of a spring tensioning element by which a spring for storage of mechanical energy, having one end fixed on said housing, can be transferred from a rest position into a tensioned position, and a moving means for said piston of said supply container, said moving means being coupled to said energy storage means and comprising a drive element coupled to the other end of said spring, said drive element being adapted to be driven, by the stored mechanical energy of said spring during the transfer from the tensioned position into the rest position of said spring, in increments so as to move a press-on element acting on said piston for displacing it in the direction of said discharge opening of said supply container.

The applicator according to the invention is provided with an energy storage means which is suited for storing mechanical energy which will then be used for dispensing a predetermined quantity of fluid. The energy storage means comprises a spring as a mechanical store, which spring can take a rest position and a tensioned position. By means of a tensioning lever pivotally supported particularly on a handle member of the housing of the applicator, the spring can be transferred from its rest position to its tensioned position. In the process, the manually initiated movement of the tensioning lever from the rest position into a pulling position is translated into a movement for transferring the spring from its rest position to its tensioned position. For this purpose, it is suitably provided that a spring tensioning element is arranged between the tensioning lever and the spring for transferring the spring into the tensioned position upon actuation of the tensioning lever.

The energy storage means has a moving means coupled thereto which comprises a movable press-on element acting on a piston of the storage container accommodating the fluid, for thus slidingly displacing the piston in the direction of the discharge opening of the storage container. Through the moving means, the press-on element is moved in increments in the moving direction, while the energy storage means transmitting its stored energy to the drive element each time when the spring moves back from its tensioned position to its rest position.

The invention provides a simple, mechanically operating mechanism allowing the discharge of fluids in doses and at an exact dosage by use of an applicator. For realizing the invention, no electric appliances and the like are required; instead, the applicator operates in a purely mechanical manner, while the energy respectively required for the discharge of fluid is supplied by a spring which is tensioned by hand.

In an advantageous embodiment of the invention, it is provided that the moving means comprises a spindle, secured against axial displacement and supported for rotation on the housing, with the spindle comprising an outer thread in threaded engagement with the inner thread of a through-hole of the press-on element. During a transfer of the spring from its tensioned position into the rest position, the thus initiated movement of the drive element is translated into a rotation of the spindle. This rotation in turn leads to a linear movement of the press-on element which is secured against being rotated along with the spindle and is guided on the housing for linear displacement. The extend of the rotational movement of the spindle caused by each relaxing of the spring and resulting in a step-wise rotation of the spring, is translated into an advance moving step of the press-on element. The extent of the advance step of the press-on element depends, among others, on the pitch of the thread of the spindle and the extend of the rotation of the spindle per relaxation of the spring.

Preferably, the pivoting movement of the tensioning lever is translated into a rotational movement of the spring tensioning element which for this purpose is supported on the housing for rotation about a rotational axis. The spring, having one end attached to the housing, has its other end eccentrically coupled to the spring tensioning element. In the rest position of the spring, the spring tensioning element is in a stable position which hereunder will be referred to as the first dead-center position. When pressing the tensioning lever by hand so that the latter is moved into its pulling position, the spring tensioning element mechanically coupled to the tensioning lever is rotated by slightly more than 180° so that the spring tensioning element is moved slightly beyond its metastabile position displaced by 180° relative to the first dead-center position (hereunder referred to as the second dead-center position). Both dead-center positions are defined in that the coupling point between the spring and the spring tensioning element are located on a common line extending in the direction of the length of the spring where also the point of the attachment of the spring on the housing is located. By the movement of the spring tensioning element beyond the metastabile dead-center position, the spring tensioning element under the influence of the spring in its tensioning position, performs a rotation by nearly 180°, and notably automatically so that the spring will then be again in its rest position wherein its spring bias acting on the spring tensioning element is lower than in its tensioned position. This second rotation of the spring tensioning element, extending over nearly 180°, is used to move the drive element for step-wise advancement of the press-on element.

Suitably, the mechanical coupling of the tensioning lever to the spring tensioning element is provided with a freewheeling function so that the tensioning lever can remain pressed when the spring tensioning element is automatically moved due to the spring force. Such a freewheeling function is suitably realized by a toothing on the spring element which extends slightly beyond 180°. This toothing meshes with a toothing of the tensioning lever or with a toothed bar moved by the lever along a linear path, with the tooth on both sides being in mutual engagement for the period of the rotational movement induced by the actuation of the tensioning lever, and then being disengaged.

As already mentioned above, the drive element and the spring tensioning element can be arranged as one element which fulfills both the function of the spring tensioning and the function of driving the press-on element. This is preferably realized in that the spring tensioning element and drive element is provided with a first toothing for meshing with a toothing of the spring tensioning lever, and with a second toothing provided to engage the toothing of an end-side pinion arranged on the spindle. While the first toothing of the spring tensioning/drive element cooperates with the spring tensioning element when the latter is manually moved from its rest position into the pulling position, the second toothing meshes with the end-side pinion of the spindle within the second half of the rotation of the spring tensioning/drive element. The positioning of this toothing and the number of teeth thereof determine the extent of the rotational movement by which the spindle moves per relaxation of the spring. Also this provides for a setting of the fluid quantity discharged per actuation of the tensioning lever which is obtained through the design.

If the drive element and the spring tensioning element are not formed as one part, both of them are suitably arranged on a common rotational axis so that the rotation of the spring tensioning element is translated into a rotation of the drive element which in turn is used for the advance movement of the press-on element.

In an advantageous embodiment of the invention, it is further provided that, simultaneously with the discharge of fluid, also a (medical) gas streams out of a gas discharge opening arranged in the immediate vicinity of the fluid discharge opening of the applicator so that the issued gas will atomize the fluid. In this regard, it is of advantage if the gas discharge period during which the gas issues from the gas discharge opening, begins prior to the fluid discharge period. Thus, the gas discharge is already underway when the fluid is discharged from the fluid discharge opening. In this manner, a formation of drops at the beginning of the fluid discharge is prevented.

Further, it is reasonable to take the same measure also around the end of the deposition process or the spray interval. In other words, gas should also be discharged from the gas discharge opening for a period, although a short one, after termination of the discharge of fluid from the gas discharge opening so that fluid drop possibly still attached to the fluid discharge opening can be deposited in sprayed form.

Within the present invention, the above described timing of gas discharge and fluid discharge in an applicator represents an independent thought which can be put to practice also in applicators of a configuration different from the one described above. Thus, this inventive thought is independently placed under protection irrespective of the applicator disclosed within the frame of the invention.

For a controlled discharge of gas in the above described applicator, the applicator is preferably provided with a gas discharge means for the controlled discharging of gas within a gas discharge period correlating with the spring-driven step-wise movement of the drive element or the actuating of the tensioning lever. Here, the gas discharge period begins earlier than the fluid discharge period during which the press-on element acting on the piston is moved. Further, it is suitable if the gas discharge period ends later than the fluid discharge period.

Preferably, the gas discharge means can be controlled by a control element which can be moved along in increments together with the drive element. Thus, the gas discharge means is controlled by the movement of the spring tensioning element and the drive element, respectively, notably indirectly through the control element.

The gas discharge means suitably is a valve arranged in a gas conduit and biased into its closing position. The valve is provided with an actuating element which is acted on by the control element for moving the valve from its closed position to its opened position. Once the control element does not act anymore on the actuating element, the valve will automatically assume its closed position.

The gas conduit having the valve arranged therein is arranged to connect a gas source for pressurized gas to a gas discharge opening. Thus, the conduit portion of the gas conduit between the gas source and the valve will always have pressurized gas therein. The further movement of this pressurized gas will thus be controlled by the valve.

Preferably, the gas supply system of the inventive applicator, comprising the gas discharge means and the gas conduit, is provided with a time-delayed switch-off characteristic, i.e. from the moment that the control element does not act anymore on the actuating element of the valve, gas will nonetheless by discharged from the gas discharge opening for a certain time. On the one hand, this can be realized in that the gas conduit between the valve and the gas discharge opening is provided with a gas storage chamber for the storage of gas. With each opening of the valve, the storage chamber is first filled with gas before gas will be discharged. This leads to a delayed discharge of gas, which, however, can be accounted for by a corresponding shifting of the point of time of the switch-on of the valve, triggered by the movement of the control element, in relation to the discharge of fluid. The advantage of the storage of pressurized gas in the storage chamber between the valve and the gas discharge opening resides in the fact that gas is discharged from the gas discharge opening for a certain period after the switch-off of the valve until the storage chamber has been emptied or its interior pressure is equal to the ambient pressure of the applicator.

A second alternative for terminating the gas discharge with a time delay resides in that the valve is moved in a time-delayed manner controlled by the pressure of the gas into its closed position when the control element does not act anymore on the actuating element of the valve.

With a valve biased into its closed position, the coupling of the control element and the actuating element can then be realized in a simple constructional manner by providing the control element as a cam to be driven by rotation and acting on the actuating element which is realized as a plunger, to thus move the plunger along a linear path against the bias of the valve. The cam is suitably rotated by the spring tensioning element and respectively the drive element of the moving means of the applicator.

An embodiment of the invention will be described in greater detail hereunder with reference to the Figures.

Figure 2:
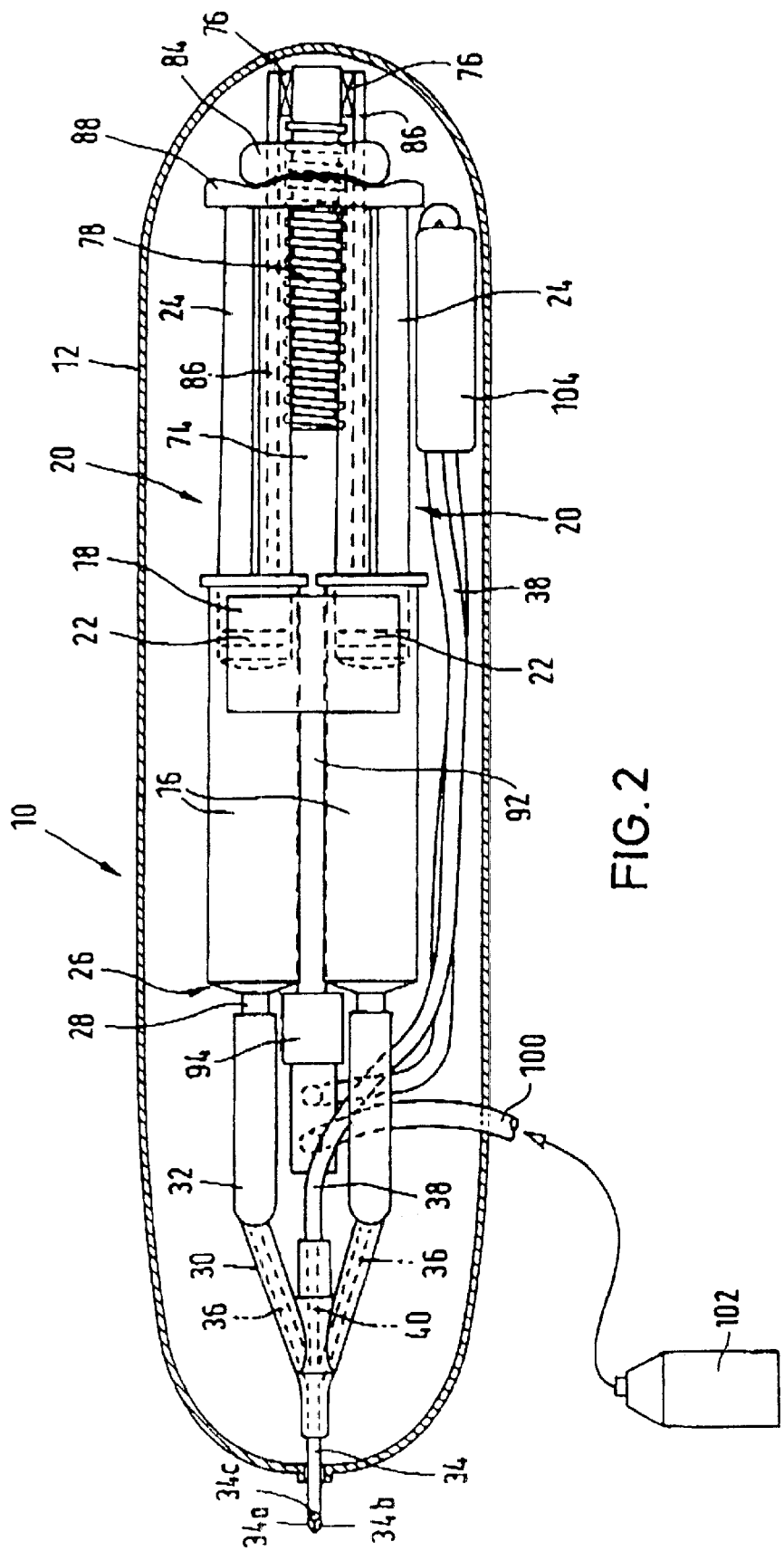
Figure 5:
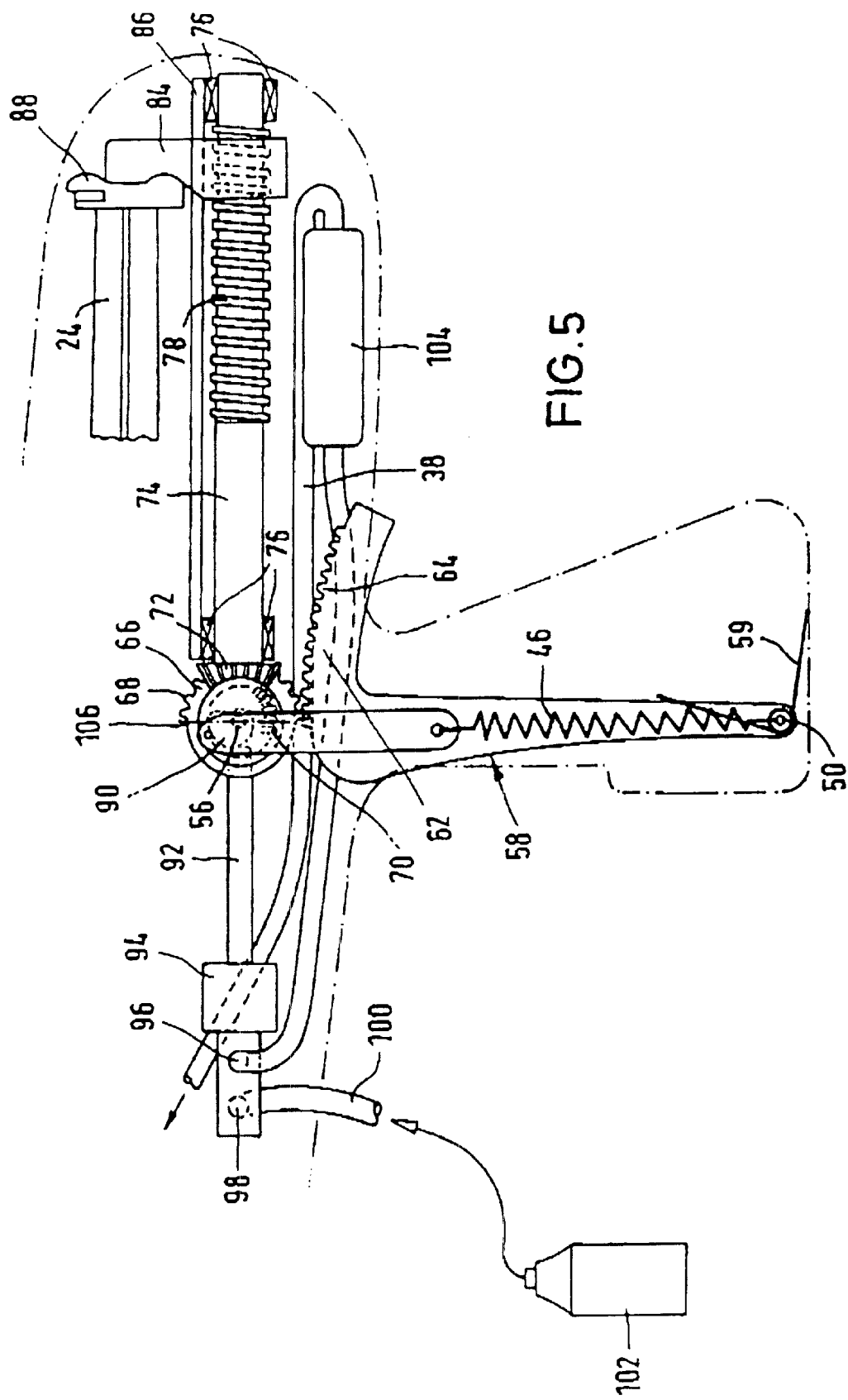
Figure 8:
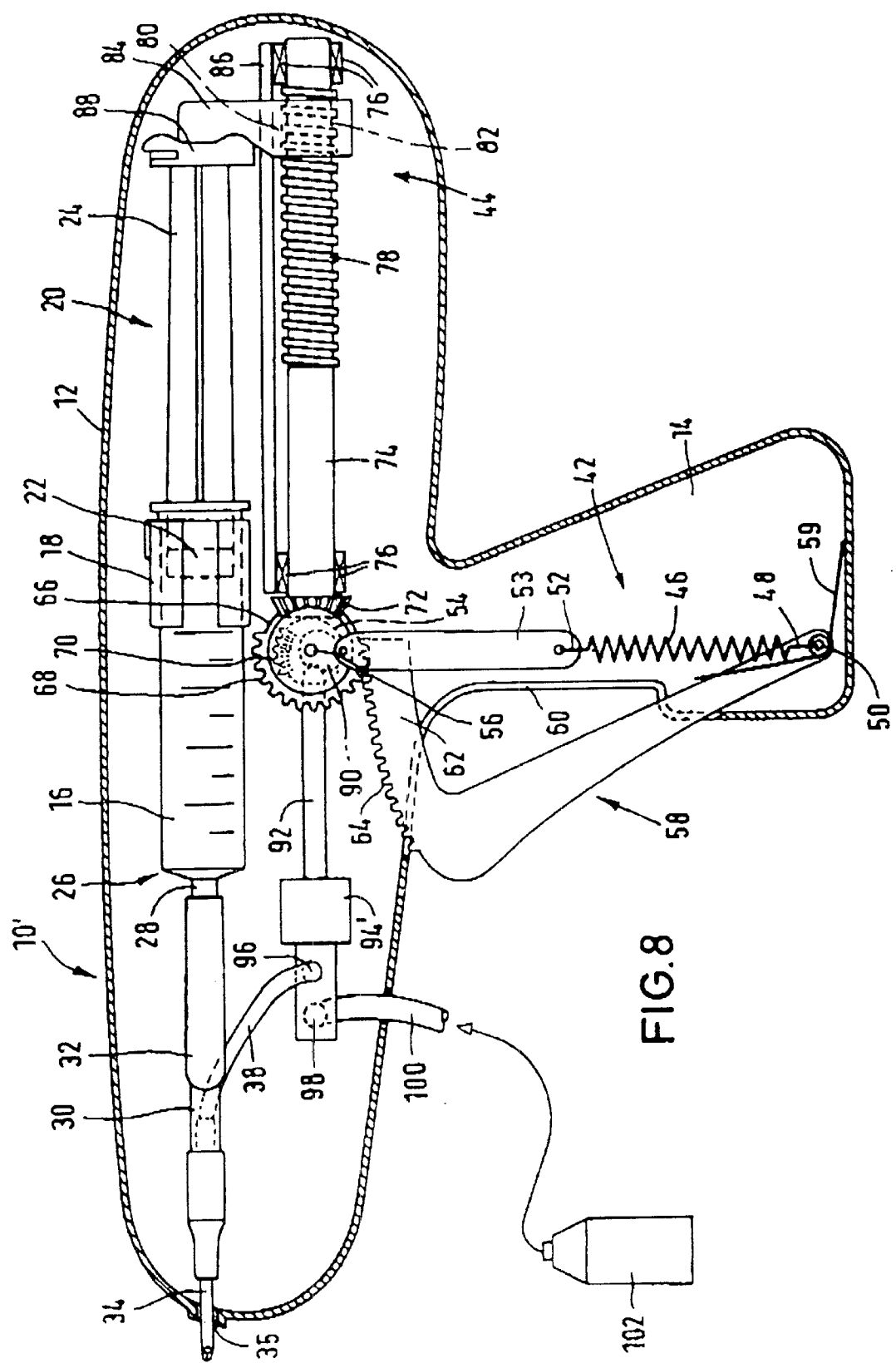
Figure 9:
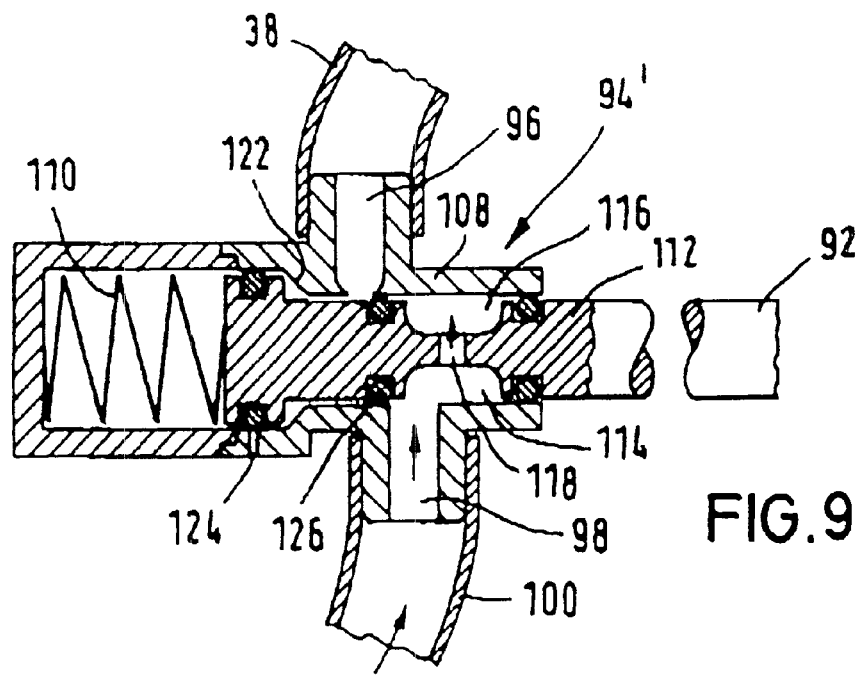

FIG. 1 is a lateral view of the applicator according to a first embodiment of the invention with the housing shown in vertical section, FIG. 2 is a horizontal sectional view of the applicator along the plane II—II in FIG. 1, FIG. 3 is a horizontal sectional view of the interior of the applicator along the plane III—III in FIG. 1, FIG. 4 is a partial view of the mechanics of the applicator along the plane IV—IV in FIG. 3, FIGS. 5 to 7 illustrate several intermediate positions of the individual elements of the mechanics of the applicator, each time seen corresponding to FIG. 4, FIG. 8 is a lateral view of an applicator according to a second embodiment of the invention, with the housing shown in vertical section, comprising a valve to be switched into its closed position at a time delay, and FIGS. 9 to 12 are sectional views of the valve of the applicator according to FIG. 8 in the closed and opened positions and an intermediate position from which the valve is switched into the closed position at a time delay.

FIG. 1 is a lateral view of an applicator 10 for discharge of the two-component tissue glue in sprayed form. Applicator 10 comprises a housing 12 with a handle 14. According to FIG. 2, the housing accommodates two supply containers in the form of two cylindrical syringe bodies 16 connected to each other through a clamping connection element 18 and held on connection element 18. Each syringe body comprises a piston 20 provided with a stopper 22 and a piston rod 24 extending therefrom. The stoppers 22 closely abut the inner wall of the supply containers 16 and are arranged for sliding displacement within the supply containers 16. Opposite the piston rods 24, the supply containers 16 have their front ends provided with respective discharge connecting pieces 28. Mounted on each of the two discharge connecting pieces 28 is a connection head member 30 having to receiving openings 32 for the discharge connecting pieces 28. Opposite the receiving openings 32, the connection head member 30 has a multi-lumen catheter 34 arranged thereon, guided out of housing 12 of applicator 10 via an opening 35. Starting at the receiving openings 32 of connection head member 30, the latter has two mutually separated channels 36 extending therethrough which enter into two lumina of multi-lumen catheter 34 which terminate in discharge openings 34a,34b on the free end of catheter 34 (FIG. 2). On the side facing towards the supply containers 16, a gas-conducting hose 38 enters into the connection head member 30. A gas-conducting channel 40 extends through the connection head from the entering site of hose 38 to catheter 34 and is flush with a further lumen of catheter 34 which ends in a gas discharge opening 34c of catheter 34.

For discharge of tissue glue from applicator 10, a pressure is exerted against the two pistons in a manner still to be described so that the tissue glue components contained in the syringe bodies 16 are discharged from the discharge openings 34a,34b via connection head member 30 and multi-lumen catheter 34. At the same time, a medical gas ($O_2$) is discharged from the third lumen of catheter 34 via gas discharge opening 34c for thus atomizing and mixing the tissue glue components so that the tissue glue can be sprayed in mixed form.

As evident particularly from FIGS. 1, 3 and 4, applicator 10 comprises a hand-actuated, purely mechanically operating mechanism by which the pistons 20 can be moved in increments in the direction of the syringe bodies 16. This mechanism comprises a mechanical energy storage means 42 and a moving means 44 for step-wise advancement of the pistons 20. Energy storage means 42 comprises a helical tensioning spring 46 having one end 48 attached to a pin 50 arranged within the handle 14 of housing 12. The other end 52 of spring 46 is connected to a connecting arm 53 which is eccentrically supported on a disk-shaped spring tensioning element 54 arranged on an axis 56 supported for rotation on housing 12. Rotatably supported on pin 50 is one end of a substantially U-shaped tensioning lever 58. By means of a leg spring 59 extending around pin 50 and supported both on lever 58 and on handle 14, lever 58 is biased into the starting or rest position shown in FIG. 1. Tensioning lever 58 partially projects from an opening 60 of housing 12 out of handle 14. The angle leg 62 of tensioning lever 58 facing away from pin 50 is provided with a toothing 64 arranged on a slightly curved line with the pin 50 as a center. This toothing 64 meshes with a pinion 67 which together with the spring tensioning element 54 is arranged for rotation on axis 56. Pinion 66 comprises a toothing 68 extending over slightly more than 180° along the circumference of pinion 60. On the remaining part of the circumference, pinion 66 does not comprise any toothing or teeth.

Pinion 66 is provided with a further toothing 70 which likewise does not extend fully along the whole circumference of pinion 66 bit instead comprises just a few teeth. This toothing 70 meshes with a conical gear 72 attached to one end of spindle 74. Spindle 74, while secured against axial displacement, is supported for rotation in housing 12 as illustrated at 76. Spindle 74 further comprises an outer thread 78 and in this region extends through a through-hole 82 having an inner thread 80 and being arranged in a press-on element 84 which is guided on guide projections 86 of housing 12 and which, upon rotation of the spindle 74, is moved along a linear path along the guide projections 86. The press-on element 84 abuts a connection element 88 connecting the ends of the piston rods 24, and via this connection element 88, acts on the two pistons 20 when the spindle 74 is driven by pinion 66.

As best seen in FIG. 3, the axis 56 is provided with a cam 90 (see the representation of the cam 90 in FIGS. 1 and 4) acting on the plunger 92 to advance it linearly and transverse to the extension of the axis 56. The plunger 92 is the actuating member of a valve 94 controlling the gas supply for the discharge of a medicinal gas and being arranged in the gas conduit 38. The gas conduit 38 extends from the outlet 96 of the valve 94 to the connector head 30. The inlet 98 of the valve 94 has a gas conduit 100 connected thereto which is connected to a (external) gas supply indicated at 102. The valve is self-closing, i.e. it is biased towards its closed position. Moving the plunger 92 in the direction of the valve 94, the latter is caused to assume its open position. Within the gas conduit 38 leading from the valve 94 to the connector head member 30, a gas reservoir 104 is provided which will be described in more detail below in connection with the description of the functions of the applicator 10.

The following is a description of the operation of the applicator 10 with reference to FIGS. 1 to 7. FIGS. 1 and 4 are partial side elevational views of the applicator 10 in the rest position prior to the manual operation of the tensioning lever 58. In this rest position, the spring tensioning element 54 is in its lower dead center position in which the coupling point between the spring-loaded connecting arm 53 and the spring tensioning element 54 is on the side of the spring tensioning element 54 that, with regard to its center, faces the pin 50. By operating the tensioning lever 58, i.e. by moving the tensioning lever 58 into the handle member 14, the toothing 64 rotates the pinion 66 and, thereby, the spring tensioning element 54 coupled therewith. This rotation of the spring tensioning element 54 caused by the tensioning lever 58 extends over slightly more than 180° (starting from the rotational position of the spring tensioning element 54 illustrated in FIG. 4) so that the coupling point between the spring-loaded connecting arm 53 and the spring tensioning element 54 has passed slightly beyond its upper dead center position. Upon reaching the upper dead center position (indicated at 106 bin FIG. 5), the spring 46 has the maximum tension and, thus, its maximum stored energy. Upon arriving at the situation illustrated in FIG. 5, I.e. with the tensioning lever 58 moved into the handle member 14 to the maximum, the toothing of the tensioning lever 58 is disengaged from the toothing 68 of the pinion 66. Due to the spring 46 contracting, the pinion 66 may move freely until the tensioning element 54 again takes its lower dead center position illustrated in FIG. 4.

Figure 6:
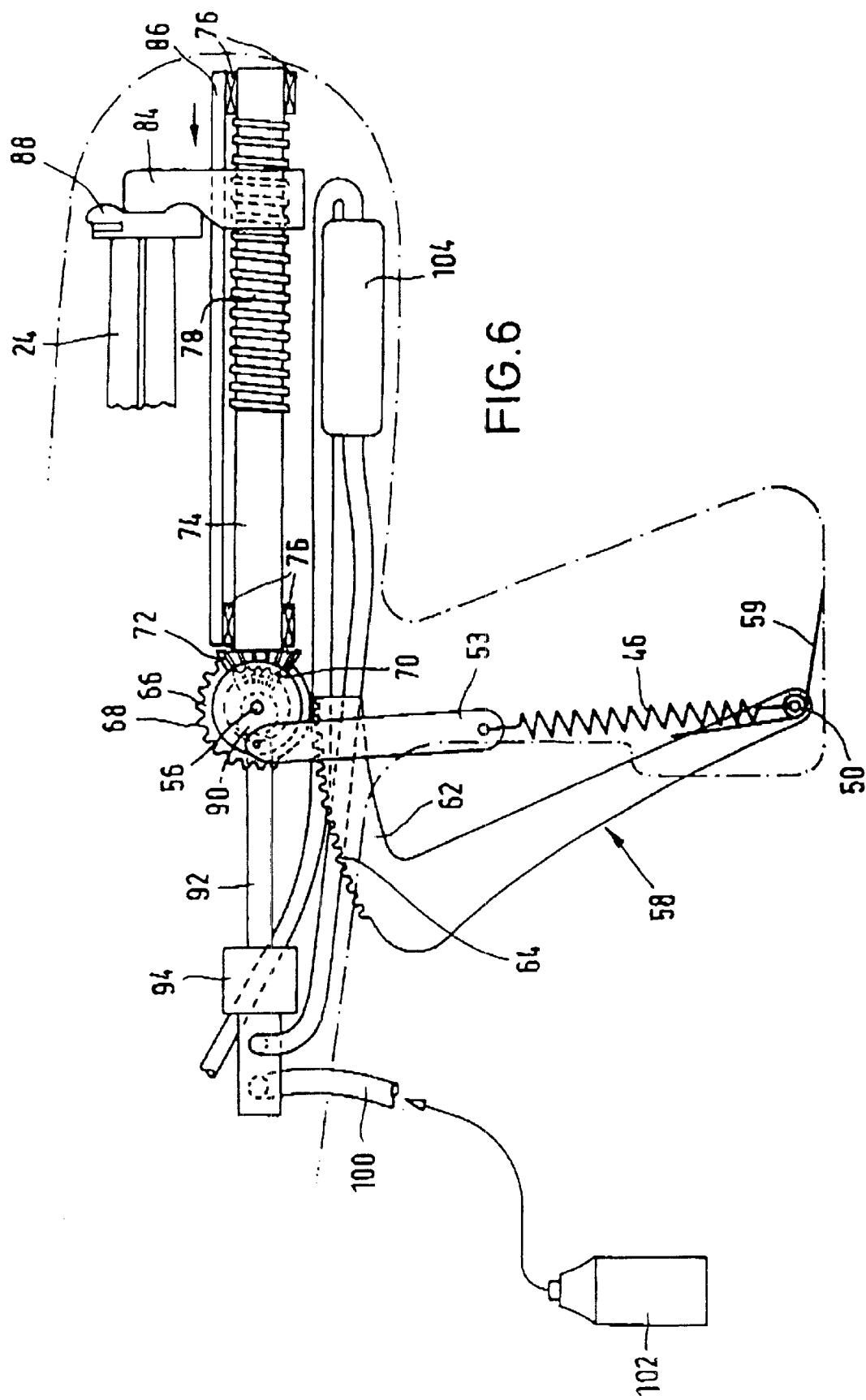
Figure 7:
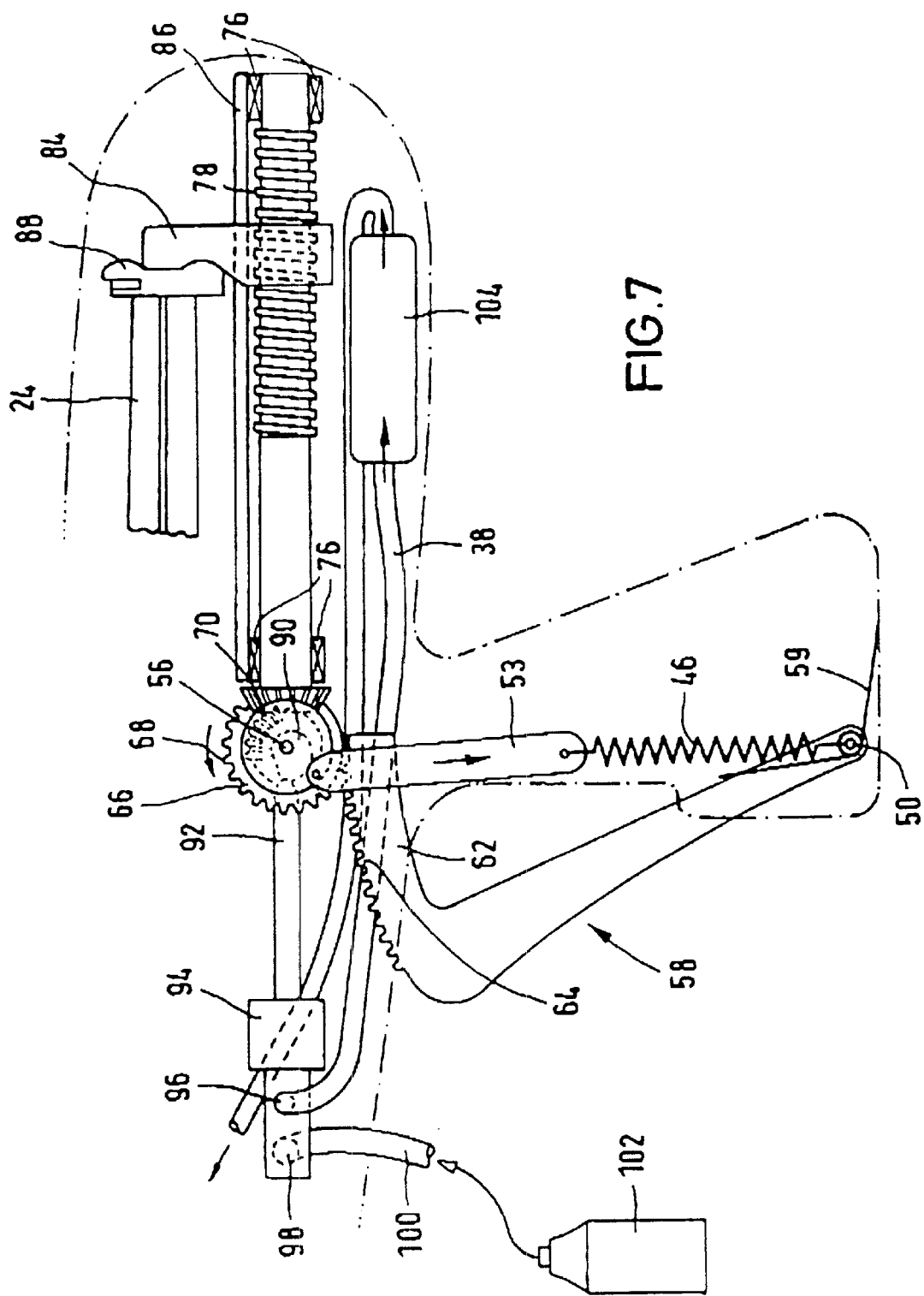

During this rotation of the pinion 66 caused by the relaxing spring, the other toothing 70 engages the conical gear 72 of the spindle 72 so that the same is rotated by an amount defined by the number of teeth in the toothing 70 (s. FIG. 6). As a consequence, the press-on element 84 is advanced linearly by a certain amount towards the syringe body 16. This, in turn, causes an amount of two-component tissue glue to be discharged that is defined by the amount of movement of the press-on element 84 and the sectional areas of the syringe bodies 16.

The above actions are repeated each time the tensioning lever 58 is actuated so that it is guaranteed that always one and the same defined amount of tissue glue is discharged every time the tensioning lever is actuated.

Besides rotating the spindle 74, the rotation of the pinion 66 also actuates the valve 94. This is effected by the cam 90 arranged on the rotational axis 56 together with the pinion 66 and operating the plunger 92. When the valve 92 is opened, pressurized gas flows into the gas conduit 38 and first fills the storage chamber 104. That means that the discharge of the gas from the catheter 34 is delayed in a manner. The relative rotational position of the cam 90 with respect to the pinion 66 is selected such that the valve 94 opens just in time before the filing of the storage chamber 104 is completed and gas flows from the catheter 34 before the spindle 74 is turned and the press-on element 84 is advanced linearly. With the completion of the linear movement of the press-on element 94, the cam 90 no longer acts upon the plunger 92 so that the valve 94 reaches its closed position. Since pressurized gas is still left in the storage chamber 104, the same escapes from the catheter 34 even after the termination of the tissue glue discharge, whereby an accumulation of tissue glue drops at the catheter 34 is prevented, which drops impair the application of the tissue glue and, possibly, could cause a clogging of the catheter 34 (see the schematic illustration in FIG. 7).

Referring now to FIGS. 8 to 12, a variation of the applicator 10' will be described below. In as far as the parts of the applicator 10 of FIGS. 1 to 7 correspond to those of the applicator 10', they have been given the same reference numerals in FIG. 8.

Figure 10:
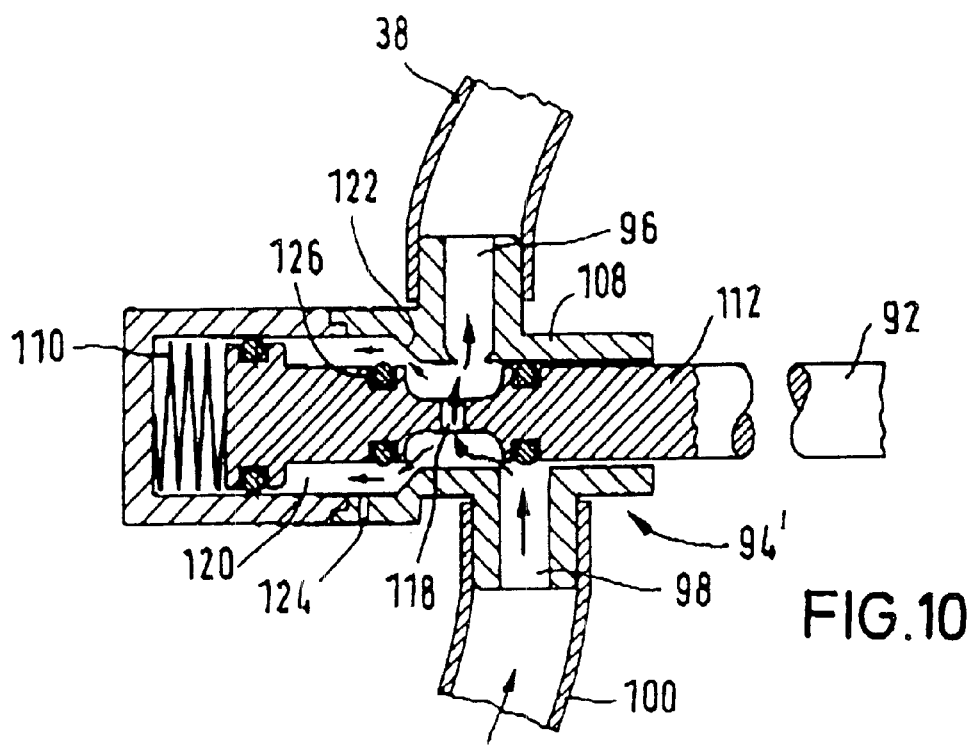
Figure 11:
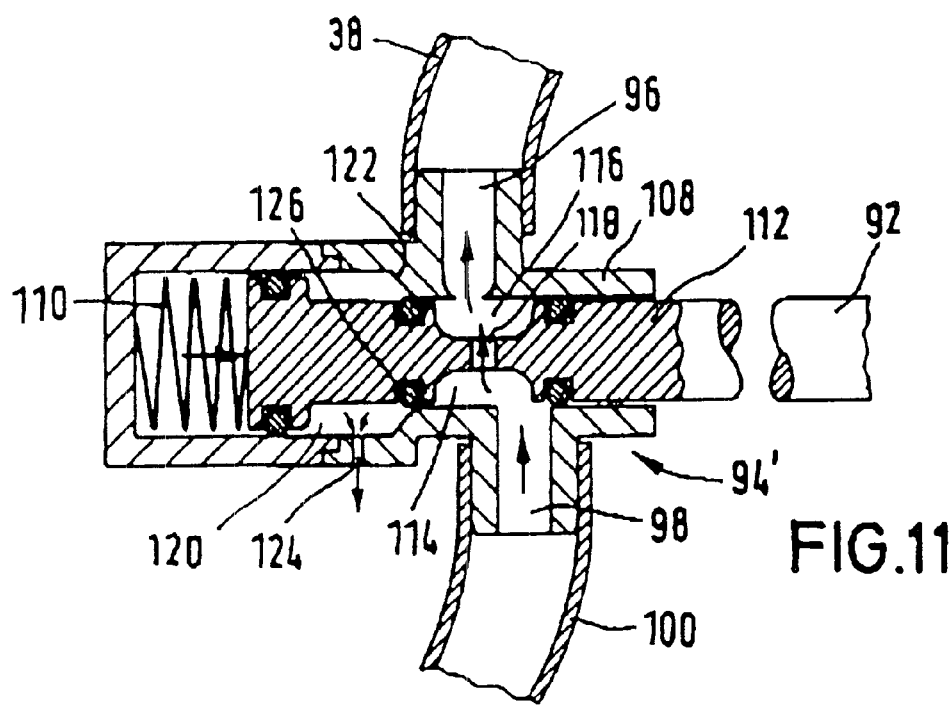

The two applicator embodiments 10, 10' differ in that the applicator 10' comprises a valve 94' which, for structure-related reasons, moves from its open position into its closed position with a delay in time. The valve 94' comprises a valve housing 108 in which a piston 112, biased towards its closed position by a pull-back spring 110, may be advanced and is guided so as to seal against the valve housing 108. The plunger 92 acts on the piston 112 projecting from valve housing 108. The valve housing 108 is provided with the inlet and outlet openings 96, 98 that are blocked, respectively, by the piston 112 in the closed position illustrated in FIGS. 9 and 12 and between which a gas connection is formed in the open position (FIGS. 10 and 11). The piston 112 has diametrically opposite edge recesses 114, 116, the edge recess 114 facing the outlet opening 98 arranged opposite the inlet opening 96. Both edge recesses 114, 116 are connected through a transverse bore 118 in the piston 112.

In the closed position, the piston 112 shuts off the outlet opening 98 of the valve housing 108 by positioning the edge recess 116 outside the outlet opening 98. When the piston 112 is moved into its open position, as illustrated in FIG. 10, the edge recesses 114, 116 will coincide with their respective associated inlet and outlet openings 96, 98 so that a gas flow communication is established via the transverse bore 118. Simultaneously, a connection is established between the inlet opening 96 and a gas storage chamber 120 formed in that portion of the valve housing 108 where the enlarged end of the piston 112 abutting the pull-back spring 110 is located. Via a shoulder 122 of the valve housing 108, this gas storage chamber 120 passes into that portion of the valve housing 108, in which the portion of the piston 112 having the edge recesses 114, 116 is located and in which the inlet and outlet openings 96, 98 are formed. The gas storage chamber 120 is connected with the environment of the valve 94 through a bore 124 in the valve housing 108 acting as a throttle.

Figure 12:
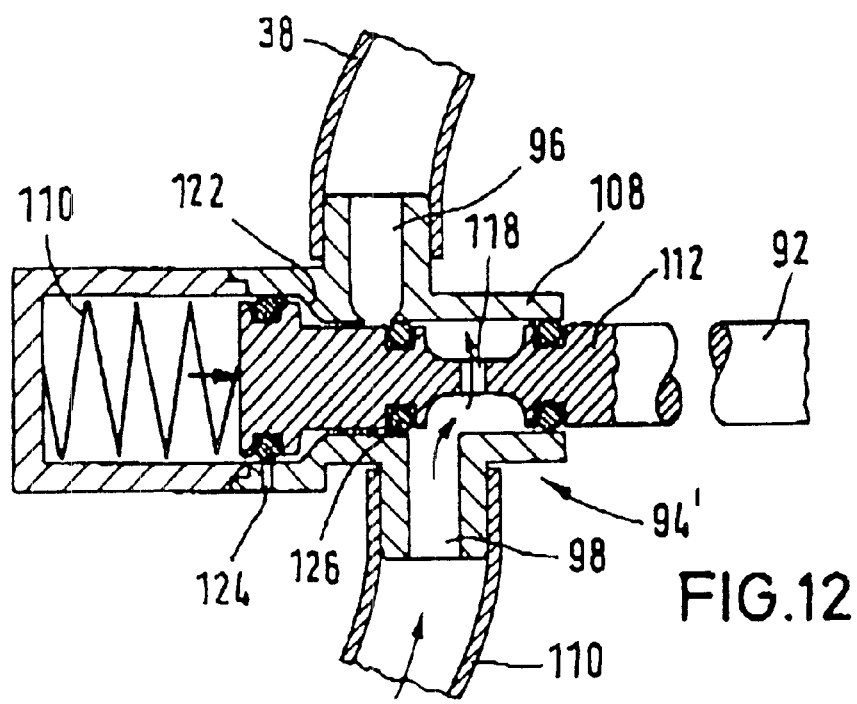

In the open position, the gas storage chamber 120 is filled with a part of the gas flowing into the valve housing 108 and being discharged via the outlet opening 98. The leak caused by the bore 124 is negligible. As soon as the plunger 92 no longer presses on the piston 112, the same moves back with the plunger 92, driven by the pull-back spring 110. The piston 112 shuts the gas storage chamber 120 off against the inlet and outlet openings 96, 98 by means of a seal ring 126 (see FIG. 11). Now, the gas from the gas storage chamber 120 can only escape through the (throttle) bore 124, causing a delay in the movement of the piston 112 to its closed position (FIG. 12). Until the closed position is reached (starting from the situation illustrated in FIG. 11), the inlet and outlet openings 96, 98 are interconnected through the transverse bore 118 so that gas keeps flowing through the valve 94'.

Thus, the structure of FIGS. 9 to 12 provides a valve with a delayed switching-off, wherein the delay in time is exclusively caused by the gas flow to be switched on and off by the valve. Therefore, no additional control lines or control media are required.

What is claimed is:

1. An applicator for depositing a one- or multi-component fluid, said applicator comprising a housing (12), at least one supply container (16) for said fluid, adapted to be mounted to said housing (12), said supply container (16) comprising a discharge opening (28) and having arranged therein a piston (20) for sliding displacement in the direction of said discharge opening (28).

an energy storage means (42) comprising a hand-operated tensioning lever (58), pivotally arranged on said housing (12), which, when moved from a rest position into a pulling position, causes movement of a spring tensioning element (54) by which a spring (46) for storage of mechanical energy, having one end (48) fixed on said housing (12), can be transferred from a rest position into a tensioned position, and a moving means (44) for the piston (20) of said supply container (16), said moving means (44) being coupled to said energy storage means (42) and comprising a drive element (66) coupled to the other end (52) of said spring (46), said drive element (66) being adapted to be driven, by the stored mechanical energy of said spring (46) during the transfer from the tensioned position into the rest position of said spring (46), in increments so as to move a press-on element (84) acting on said piston (20) for displacing it in the direction of said discharge opening (28) of said supply container (16).

2. The applicator according to claim 1, characterized in that said moving means (44) comprises a spindle (74), secured against axial displacement and supported for rotation on said housing (12), which spindle (74) comprises a thread (78) being in threaded engagement with said press-on element (84), said press-on element (84) being guided for linear displacement on said housing (12) while being secured against rotation along with said spindle (74), and that the stored energy of said spring (46) can be transformed by said drive element (66) into an incremental rotational movement of said spindle (74).

3. The applicator according to claim 1, characterized in that said spring tensioning element (54) is supported on said housing (12) for rotation about a rotational axis (56) and is eccentrically coupled to said spring (46), and that, upon actuation of said tensioning lever (58), said spring tensioning element (54) can be rotated from a first dead-center position in which said spring (46) takes a rest position wherein it is less tensioned than in its tensioned position, up to slightly beyond a second dead-center position, rotated by about 180° relatively to said first dead-center position, in which said spring (46) is in its tensioned position and from which said spring tensioning element (54) can be automatically rotated onwards into said first dead-center position due to the mechanical energy stored in said spring (46).

4. The applicator according to claim 3, characterized in that said spring tensioning element (54) and/or said drive element (66) comprises a toothing (68), extending slightly beyond 180°, for meshing with a toothing (64) of said tensioning lever (58), both of said toothings (64, 68) being in engagement with each other for rotating said spring tensioning element (54) from said first dead-center position up to slightly beyond said engagement during the subsequent automatic rotation of said spring tensioning element (54) back into said first dead-center position.

5. The applicator according to claim 3, characterized in that said drive element (66) and said spring tensioning element (54) are arranged on a common rotational axis (56).

6. The applicator according to claim 3, characterized in that said drive element (66) comprises a toothing (70) for meshing with a toothing (72) of said spindle (74).

7. The applicator according to claim 6, characterized in that the amount of said increments of the rotation of said spindle (74) can be set by the number and arrangement of the teeth of said toothing (70,72) of said drive element (66) and/or of said spindle (74).

8. The applicator according to claim 1, characterized in that said drive element (66) and said spring tensioning element (54) are formed integrally.

9. The applicator according to claim 1, characterized in that a gas discharge means (94;941) is provided for the discharge of gas within a gas-discharge time period correlated with the spring-driven incremental movement of said drive element (66) or the actuation of said tensioning lever (58), said gas discharge time period starting earlier and ending later than a fluid-discharge time period during which said press-on element (84) acting on said piston (20) is moving.

10. The applicator according to claim 9, characterized in that said gas discharge means (94;941) can be driven by a control element (90) which is movable by said spring tensioning element (54) and/or said drive element (66).

11. The applicator according to claim 10, characterized in that said control element (90) is a cam member (90) rotatably driven by said drive element (66) and/or said spring tensioning element (54) and cooperating with the actuating element (92) of said valve, said actuating element (92) being shaped as a plunger.

12. The applicator according to claim 9, characterized in that said gas discharge means (94; 94') is a valve biased into its closed position and comprising an actuating element (92) which is acted on by said control element (90) during its movement caused by said drive element (66) and/or said spring tensioning element (54) so as to move said valve from its closed position into its opened position.

13. The applicator according to claim 12, characterized in that said valve is arranged in a gas conduit (38,100) guiding pressurized gas, said gas conduit (38,100) connecting a gas source (102) to a gas discharge opening (catheter 34).

14. The applicator according to claim 13, characterized in that a storage chamber (104) for the storage of gas is arranged in said gas conduit (38,100) between said valve and said gas discharge opening (catheter 34), the gas contained in said storage chamber (104) still flowing out of said gas discharge opening (catheter 34) for a controlled time period after the closing of said valve.

15. The applicator according to claim 13, characterized in that said valve is configured in a manner allowing it to be moved into the closed position with a time delay while controlled by the pressure of said gas.

16. The applicator of claim 1, wherein said applicator is a tissue adhesive applicator which further comprises tissue adhesive.

17. An applicator for depositing a one- or multicomponent fluid, said applicator comprising (A) a housing (123), (B) at least one supply container (16) for said fluid, adapted to be mounted to said housing (12), said supply container (16) comprising a discharge opening (28) and having arranged therein a piston (20) for sliding displacement in the direction of said discharge opening (28), (C) spring (42) comprising a hand-operated tensioning lever (58), pivotally arranged on said housing (12), which, when moved from a rest position into a pulling position, causes movement of a spring tensioning element (54) by which a spring (46) for storage of mechanical energy, having one end (48) fixed on said housing (12), can be transferred from a rest position into a tensioned position, and (D) a spindle (44) for the piston (20) of said supply container (16), said spindle (44) being coupled to (C) and comprising a drive element (66)coupled to the other end (52) of said spring (46), said drive element (66) being adapted to be driven, by the stored mechanical energy of said spring (46) during the transfer from the tensioned position into the rest position of said spring (46), in increments so as to move a press-on element (84) acting on said piston (20) for displacing it in the direction of said discharge opening (28) of said supply container (16).

18. The applicator of claim 17, wherein said applicator is a tissue adhesive applicator which further comprises tissue adhesive.

* * * * *